(12) United States Patent
Brammer et al.

(10) Patent No.: US 10,292,424 B2
(45) Date of Patent: May 21, 2019

(54) AEROSOL DELIVERY DEVICE INCLUDING A PRESSURE-BASED AEROSOL DELIVERY MECHANISM

(71) Applicant: R.J. Reynolds Tobacco Company, Winston-Salem, NC (US)

(72) Inventors: David Allan Brammer, Smyrna, GA (US); David Jackson, Gainesville, GA (US); Nigel John Flynn, Flowery Branch, GA (US); Eric T. Hunt, Pfafftown, NC (US); Stephen Benson Sears, Siler City, NC (US); Dennis Lee Potter, Kernersville, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 383 days.

(21) Appl. No.: 14/289,101

(22) Filed: May 28, 2014

(65) Prior Publication Data

US 2015/0117841 A1 Apr. 30, 2015

Related U.S. Application Data

(60) Provisional application No. 61/897,917, filed on Oct. 31, 2013.

(51) Int. Cl.
*A61M 15/06* (2006.01)
*F24H 1/00* (2006.01)
(Continued)

(52) U.S. Cl.
CPC ......... *A24F 47/008* (2013.01); *A61M 11/007* (2014.02); *A61M 15/025* (2014.02);
(Continued)

(58) Field of Classification Search
CPC ....... H05B 3/02; A61M 15/025; A61M 15/06; A24F 47/008; F24H 1/0018
(Continued)

(56) References Cited

U.S. PATENT DOCUMENTS

| 1,771,366 A | 7/1930 | Wyss et al. |
| 2,057,353 A | 10/1936 | Whittemore, Jr. |

(Continued)

FOREIGN PATENT DOCUMENTS

| AU | 276250 | 7/1965 |
| CA | 2 641 869 | 5/2010 |

(Continued)

OTHER PUBLICATIONS

International Search Report and Written Opinion of the International Searching Authority for corresponding International Application No. PCT/US2014/062835 dated Feb. 10, 2015.

(Continued)

*Primary Examiner* — Thor S Campbell
(74) *Attorney, Agent, or Firm* — Womble Bond Dickinson (US) LLP (57) ABSTRACT

The present disclosure relates to aerosol delivery devices. The aerosol delivery devices include mechanisms configured to deliver an aerosol precursor composition from a reservoir to an atomizer including a heating element to produce a vapor. A pressure controller may control dispensing of the aerosol precursor composition from the reservoir based on a pressure differential between a first pressure within the reservoir and a second pressure proximate the atomizer. The first pressure within the reservoir may be substantially equal to atmospheric pressure. Alternatively, the first pressure within the reservoir may be greater than atmospheric pressure.

20 Claims, 7 Drawing Sheets

(51) Int. Cl.
*H05B 3/02* (2006.01)
*A24F 47/00* (2006.01)
*A61M 11/00* (2006.01)
*A61M 15/02* (2006.01)
*A61M 11/04* (2006.01)
*A61M 16/00* (2006.01)

(52) U.S. Cl.
CPC ........... *A61M 15/06* (2013.01); *F24H 1/0018* (2013.01); *H05B 3/02* (2013.01); *A61M 11/042* (2014.02); *A61M 2016/0024* (2013.01); *A61M 2205/8206* (2013.01)

(58) Field of Classification Search
USPC ............... 392/386, 387, 390, 394, 397, 398, 392/400–404
See application file for complete search history.

(56) References Cited

U.S. PATENT DOCUMENTS

| | | |
|---|---|---|
| 2,104,266 A | 1/1938 | McCormick |
| 3,200,819 A | 8/1965 | Gilbert |
| 4,284,089 A | 8/1981 | Ray |
| 4,303,083 A | 12/1981 | Burruss, Jr. |
| 4,735,217 A | 4/1988 | Gerth et al. |
| 4,848,374 A | 7/1989 | Chard et al. |
| 4,907,606 A | 3/1990 | Lilja et al. |
| 4,922,901 A | 5/1990 | Brooks et al. |
| 4,945,931 A | 8/1990 | Gori |
| 4,947,874 A | 8/1990 | Brooks et al. |
| 4,947,875 A | 8/1990 | Brooks et al. |
| 4,986,286 A | 1/1991 | Roberts et al. |
| 5,019,122 A | 5/1991 | Clearman et al. |
| 5,042,510 A | 8/1991 | Curtiss et al. |
| 5,060,671 A | 10/1991 | Counts et al. |
| 5,093,894 A | 3/1992 | Deevi et al. |
| 5,144,962 A | 8/1992 | Counts et al. |
| 5,249,586 A | 10/1993 | Morgan et al. |
| 5,261,424 A | 11/1993 | Sprinkel, Jr. |
| 5,322,075 A | 6/1994 | Deevi et al. |
| 5,353,813 A | 10/1994 | Deevi et al. |
| 5,369,723 A | 11/1994 | Counts et al. |
| 5,372,148 A | 12/1994 | McCafferty et al. |
| 5,388,574 A | 2/1995 | Ingebrethsen et al. |
| 5,408,574 A | 4/1995 | Deevi et al. |
| 5,468,936 A | 11/1995 | Deevi et al. |
| 5,498,850 A | 3/1996 | Das |
| 5,515,842 A | 5/1996 | Ramseyer et al. |
| 5,530,225 A | 6/1996 | Hajaligol |
| 5,564,442 A | 10/1996 | MacDonald et al. |
| 5,649,554 A | 7/1997 | Sprinkel et al. |
| 5,666,977 A | 9/1997 | Higgins et al. |
| 5,687,746 A | 11/1997 | Rose et al. |
| 5,726,421 A | 3/1998 | Fleischhauer et al. |
| 5,727,571 A | 3/1998 | Meiring et al. |
| 5,743,251 A | 4/1998 | Howell et al. |
| 5,799,663 A | 9/1998 | Gross et al. |
| 5,819,756 A | 10/1998 | Mielordt |
| 5,865,185 A | 2/1999 | Collins et al. |
| 5,865,186 A | 2/1999 | Volsey, II |
| 5,878,752 A | 3/1999 | Adams et al. |
| 5,894,841 A | 4/1999 | Voges |
| 5,934,289 A | 8/1999 | Watkins et al. |
| 5,954,979 A | 9/1999 | Counts et al. |
| 5,967,148 A | 10/1999 | Harris et al. |
| 6,040,560 A | 3/2000 | Fleischhauer et al. |
| 6,053,176 A | 4/2000 | Adams et al. |
| 6,089,857 A | 7/2000 | Matsuura et al. |
| 6,095,153 A | 8/2000 | Kessler et al. |
| 6,125,853 A | 10/2000 | Susa et al. |
| 6,155,268 A | 12/2000 | Takeuchi |
| 6,164,287 A | 12/2000 | White |
| 6,196,218 B1 | 3/2001 | Voges |
| 6,196,219 B1 | 3/2001 | Hess et al. |
| 6,234,167 B1 | 5/2001 | Cox et al. |
| 6,501,052 B2 | 12/2002 | Cox et al. |
| 6,601,776 B1 | 8/2003 | Oljaca et al. |
| 6,615,840 B1 | 9/2003 | Fournier et al. |
| 6,688,313 B2 | 2/2004 | Wrenn et al. |
| 6,772,756 B2 | 8/2004 | Shayan |
| 6,803,545 B2 | 10/2004 | Blake et al. |
| 6,854,461 B2 | 2/2005 | Nichols |
| 6,854,470 B1 | 2/2005 | Pu |
| 7,117,867 B2 | 10/2006 | Cox et al. |
| 7,293,565 B2 | 11/2007 | Griffin et al. |
| 7,311,503 B2 | 12/2007 | Van Lintel et al. |
| 7,513,253 B2 | 4/2009 | Kobayashi et al. |
| 7,775,459 B2 | 8/2010 | Martens, III et al. |
| 7,832,410 B2 | 11/2010 | Hon |
| 7,845,359 B2 | 12/2010 | Montaser |
| 7,896,006 B2 | 3/2011 | Hamano et al. |
| 8,127,772 B2 | 3/2012 | Montaser |
| 8,156,944 B2 | 4/2012 | Han |
| 8,314,591 B2 | 11/2012 | Terry et al. |
| 8,365,742 B2 | 2/2013 | Hon |
| 8,393,331 B2 | 3/2013 | Hon |
| 8,402,976 B2 | 3/2013 | Fernando et al. |
| 8,490,628 B2 | 7/2013 | Hon |
| 8,499,766 B1 | 8/2013 | Newton |
| 8,528,569 B1 | 9/2013 | Newton |
| 8,550,069 B2 | 10/2013 | Alelov |
| 2002/0146242 A1 | 10/2002 | Vieira |
| 2003/0108342 A1* | 6/2003 | Sherwood ............ A61M 11/041 392/397 |
| 2003/0226837 A1 | 12/2003 | Blake et al. |
| 2004/0118401 A1 | 6/2004 | Smith et al. |
| 2004/0129280 A1 | 7/2004 | Woodson et al. |
| 2004/0200488 A1 | 10/2004 | Felter et al. |
| 2004/0226568 A1 | 11/2004 | Takeuchi et al. |
| 2005/0016550 A1 | 1/2005 | Katase |
| 2006/0016453 A1 | 1/2006 | Kim |
| 2006/0196518 A1 | 9/2006 | Hon |
| 2007/0074734 A1 | 4/2007 | Braunshteyn et al. |
| 2007/0102013 A1 | 5/2007 | Adams et al. |
| 2007/0215167 A1 | 9/2007 | Crooks et al. |
| 2008/0085103 A1 | 4/2008 | Beland et al. |
| 2008/0092912 A1 | 4/2008 | Robinson et al. |
| 2008/0257367 A1 | 10/2008 | Paterno et al. |
| 2008/0276947 A1 | 11/2008 | Martzel |
| 2008/0302374 A1 | 12/2008 | Wengert et al. |
| 2009/0095311 A1 | 4/2009 | Hon |
| 2009/0095312 A1 | 4/2009 | Herbrich et al. |
| 2009/0126745 A1 | 5/2009 | Hon |
| 2009/0188490 A1 | 7/2009 | Hon |
| 2009/0230117 A1 | 9/2009 | Fernando et al. |
| 2009/0272379 A1 | 11/2009 | Thorens et al. |
| 2009/0283103 A1 | 11/2009 | Nielsen et al. |
| 2009/0320863 A1 | 12/2009 | Fernando et al. |
| 2010/0043809 A1 | 2/2010 | Magnon |
| 2010/0083959 A1 | 4/2010 | Siller |
| 2010/0200006 A1 | 8/2010 | Robinson et al. |
| 2010/0229881 A1 | 9/2010 | Hearn |
| 2010/0242974 A1 | 9/2010 | Pan |
| 2010/0307518 A1 | 12/2010 | Wang |
| 2010/0313901 A1 | 12/2010 | Fernando et al. |
| 2011/0005535 A1 | 1/2011 | Xiu |
| 2011/0011396 A1 | 1/2011 | Fang |
| 2011/0036363 A1 | 2/2011 | Urtsev et al. |
| 2011/0036365 A1 | 2/2011 | Chong et al. |
| 2011/0094523 A1 | 4/2011 | Thorens et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0168194 A1 | 7/2011 | Hon |
| 2011/0265806 A1 | 11/2011 | Alarcon et al. |
| 2011/0309157 A1 | 12/2011 | Yang et al. |
| 2012/0042885 A1 | 2/2012 | Stone et al. |
| 2012/0060853 A1 | 3/2012 | Robinson et al. |
| 2012/0111347 A1 | 5/2012 | Hon |
| 2012/0132643 A1 | 5/2012 | Choi et al. |
| 2012/0227752 A1 | 9/2012 | Alelov |
| 2012/0231464 A1 | 9/2012 | Yu et al. |
| 2012/0260927 A1 | 10/2012 | Liu |

(56) References Cited

U.S. PATENT DOCUMENTS

| | | |
|---|---|---|
| 2012/0279512 A1 | 11/2012 | Hon |
| 2012/0318882 A1 | 12/2012 | Abehasera |
| 2013/0037041 A1 | 2/2013 | Worm et al. |
| 2013/0056013 A1 | 3/2013 | Terry et al. |
| 2013/0081623 A1 | 4/2013 | Buchberger |
| 2013/0081625 A1 | 4/2013 | Rustad et al. |
| 2013/0081642 A1 | 4/2013 | Safari |
| 2013/0192619 A1 | 8/2013 | Tucker et al. |
| 2013/0306084 A1 | 11/2013 | Flick |
| 2013/0319439 A1 | 12/2013 | Gorelick et al. |
| 2013/0340750 A1 | 12/2013 | Thorens et al. |
| 2013/0340775 A1 | 12/2013 | Juster et al. |
| 2014/0060554 A1 | 3/2014 | Collett et al. |
| 2014/0060555 A1 | 3/2014 | Chang et al. |
| 2014/0096781 A1 | 4/2014 | Sears et al. |
| 2014/0096782 A1 | 4/2014 | Ampolini et al. |
| 2015/0114411 A1 | 4/2015 | Buchberger |
| 2016/0037826 A1 | 2/2016 | Hearn et al. |
| 2016/0106154 A1 | 4/2016 | Lord |

FOREIGN PATENT DOCUMENTS

| | | |
|---|---|---|
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201199922 Y | 3/2009 |
| CN | 201273820 Y | 7/2009 |
| CN | 201379072 | 1/2010 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2 218 760 | 8/2010 |
| EP | 2 316 286 | 5/2011 |
| GB | 2469850 | 11/2010 |
| WO | WO 1997/48293 | 12/1997 |
| WO | WO 2004/043175 | 5/2004 |
| WO | WO 2005/099494 | 10/2005 |
| WO | WO 2005/120614 | 12/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | WO 2012/072762 | 6/2012 |
| WO | WO 2012/100523 | 8/2012 |
| WO | WO 2013/089551 | 6/2013 |

OTHER PUBLICATIONS

The Lee Company; Electro-Fluidic Systems—Solenoid Valves; website visited Aug. 7, 2014 http://www.theleeco.com/electro-fluidic-systems/solenoid-valves/solenoid-valves.cfm.

State Intellectual Property Office of People's Republic of China, Notification of First Office Action, Application No. 201480071512.5, dated Feb. 2, 2018.

* cited by examiner

AEROSOL DELIVERY DEVICE INCLUDING A PRESSURE-BASED AEROSOL DELIVERY MECHANISM

CROSS-REFERENCE TO RELATED APPLICATIONS

This application claims the benefit of U.S. Provisional Application No. 61/897,917; filed Oct. 31, 2013, which is incorporated herein by reference in its entirety.

FIELD OF THE DISCLOSURE

The present disclosure relates to aerosol delivery devices, such as smoking articles; and more particularly, to aerosol delivery devices that utilize electrically generated heat for the production of aerosol (e.g., smoking articles commonly referred to as electronic cigarettes). Aerosol delivery devices including mechanisms for delivery of an aerosol precursor composition to an atomizer are provided. The smoking articles may be configured to heat an aerosol precursor, which may incorporate materials made or derived from tobacco or otherwise incorporate tobacco, capable of vaporizing to form an inhalable aerosol for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al. and U.S. Pat. Pub. Nos. 2013/0255702 to Griffith, Jr. et al. and 2014/0096781 to Sears et al., which are incorporated herein by reference. See also, for example, the various types of smoking articles, aerosol delivery devices and electrically powered heat generating sources referenced by brand name and commercial source in U.S. patent application Ser. No. 14/170,838, filed Feb. 3, 2014, to Bless et al., which is incorporated herein by reference.

However, it may be desirable to provide aerosol delivery devices with enhanced functionality. In this regard, it may be desirable to improve delivery of an aerosol precursor composition to an atomizer.

BRIEF SUMMARY OF THE DISCLOSURE

The present disclosure relates to aerosol delivery systems. Such systems have the ability to generate aerosol as a result of heat generated by electrical power sources, and to deliver aerosol that is intended to be drawn into the mouth of a user. Of particular interest are aerosol delivery systems that provide components of tobacco in an aerosol form, such as is provided to smokers by devices commonly known or characterized as electronic cigarettes. As used herein, term "aerosol" is meant to include vapors, gases and aerosols of a form or type suitable for human inhalation, whether or not visible, and whether or not of a form that might be considered to be "smoke-like."

Various embodiments of mechanisms for delivering an aerosol precursor composition to an atomizer are provided. These mechanisms may include pumps, passively puff-induced delivery of the aerosol precursor composition, pressurized aerosol precursor reservoirs, bubble jet heads, and other mechanisms as described hereinafter.

In one aspect an aerosol delivery device is provided. The aerosol delivery device may include a control body and a cartridge including a reservoir at least partially filled with an aerosol precursor composition. The cartridge may be configured to receive an airflow from the control body. The aerosol delivery device may additionally include an atomizer including a heating element. Further, the aerosol delivery device may include a pressure controller configured to control dispensing of the aerosol precursor composition from the reservoir based on a pressure differential between a first pressure within the reservoir and a second pressure proximate the atomizer. The atomizer may be configured to heat the aerosol precursor composition received from the reservoir to add an aerosol to the airflow.

In some embodiments the first pressure within the reservoir may be greater than an ambient pressure. The pressure controller may include a valve configured to selectively release the aerosol precursor composition from the reservoir. The aerosol delivery device may additionally include a flow sensor, and the valve may be configured to actuate in response to a signal from the flow sensor.

In some embodiments the cartridge may include the valve and the atomizer. In another embodiment the control body may include the valve and the atomizer. The control body may include a coupler and the cartridge may include a base. The valve may be in fluid communication with the reservoir when the coupler of the control body is coupled to the base of the cartridge.

In some embodiments the first pressure within the reservoir may be substantially equal to an ambient pressure. The pressure controller may include a flow restrictor configured to produce the pressure differential between the first pressure within the reservoir and the second pressure proximate the atomizer. The control body may include the flow restrictor. The flow restrictor may include one or more restrictor apertures.

In some embodiments the reservoir may include an aerosol precursor bag. The atomizer may additionally include a fluid delivery tube configured to deliver the aerosol precursor composition from the reservoir to the heating element during application of the pressure differential and otherwise resist flow of the aerosol precursor composition to the heating element. The atomizer may define a chamber and the heating element may be positioned within the chamber.

In an additional aspect a method for aerosolization in an aerosol delivery device is provided. The method may include directing an airflow from a control body through a cartridge including a reservoir at least partially filled with an aerosol precursor composition, controlling dispensing of the aerosol precursor composition from the reservoir to an atomizer including a heating element based on a pressure differential between a first pressure within the reservoir and a second pressure proximate the atomizer, and heating the aerosol precursor composition dispensed from the reservoir with the heating element to add an aerosol to the airflow.

In some embodiments the first pressure within the reservoir may be greater than an ambient pressure. Further, controlling dispensing of the aerosol precursor composition may include selectively releasing the aerosol precursor composition from the reservoir with a valve. The method may additionally include detecting an airflow with a flow sensor. Controlling dispensing of the aerosol precursor composition may include actuating the valve in response to a signal from the flow sensor. Selectively releasing the aerosol precursor composition from the reservoir with the valve may include directing the aerosol precursor composition from the reservoir in the cartridge through the valve in the control body.

In some embodiments an internal pressure within the reservoir may be substantially equal to an ambient pressure. Controlling dispensing of the aerosol precursor composition may include producing the pressure differential between the first pressure within the reservoir and the second pressure proximate the atomizer with a flow restrictor. The method may additionally include delivering the aerosol precursor composition through a fluid delivery tube to the heating element during application of the pressure differential and otherwise resisting flow of the aerosol precursor composition to the heating element. Controlling dispensing of the aerosol precursor composition may include directing the aerosol precursor composition to a chamber of the atomizer in which the heating element is positioned.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

BRIEF DESCRIPTION OF THE FIGURES

Having thus described the disclosure in the foregoing general terms, reference will now be made to the accompanying drawings, which are not necessarily drawn to scale, and wherein:

DETAILED DESCRIPTION OF PREFERRED EMBODIMENTS

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural variations unless the context clearly dictates otherwise.

As described hereinafter, embodiments of the present disclosure relate to aerosol delivery systems, devices, and components therefor. Aerosol delivery systems according to the present disclosure use electrical energy to heat a material (preferably without combusting the material to any significant degree) to form an inhalable substance; and components of such systems have the form of articles that are most preferably sufficiently compact to be considered hand-held devices. That is, use of components of preferred aerosol delivery systems does not result in the production of smoke in the sense that aerosol results principally from by-products of combustion or pyrolysis of tobacco, but rather, use of those preferred systems results in the production of vapors resulting from volatilization or vaporization of certain components incorporated therein. In preferred embodiments, components of aerosol delivery systems may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery systems may provide many of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like.

Aerosol delivery systems of the present disclosure also can be characterized as being suitable vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas).

Aerosol delivery systems of the present disclosure most preferably comprise some combination of a power source (i.e., an electrical power source), at least one control component (e.g., means for actuating, controlling, regulating and/or ceasing power supplied for heat generation, such as by controlling electrical current flow from an electrical power release unit to other components of the aerosol generating piece), a heater or heat generation component (e.g., an electrical resistance heating element and related components commonly referred to as providing an "atomizer"), and an aerosol precursor (e.g., a composition that commonly is a liquid capable of yielding an aerosol upon application of sufficient heat, such as ingredients commonly referred to as "smoke juice," "e-liquid" and "e-juice"), and a mouthend region or tip for allowing draw upon the aerosol delivery device for aerosol inhalation (e.g., a defined air flow path through the aerosol generation piece such that aerosol generated can be withdrawn therefrom upon draw). Exemplary formulations for aerosol precursor materials that may be used according to the present disclosure are described in U.S. Pat. Pub. No. 2013/0008457 to Zheng et al., the disclosure of which is incorporated herein by reference in its entirety.

More specific formats, configurations and arrangements of components within the aerosol delivery systems of the present disclosure will be evident in light of the further disclosure provided hereinafter. Additionally, the selection and arrangement of various aerosol delivery system components can be appreciated upon consideration of the commercially available electronic aerosol delivery devices, such as those representative products referenced in background art section of the present disclosure.

Alignment of the components within the aerosol delivery device can vary. In specific embodiments, the aerosol precursor composition can be located near an end of the article (e.g., within a cartridge, which in certain circumstances can be replaceable and disposable), which may be configured to be positioned proximal to the mouth of a user so as to maximize aerosol delivery to the user. Other configurations, however, are not excluded. Generally, the heating element can be positioned sufficiently near the aerosol precursor composition so that heat from the heating element can volatilize the aerosol precursor composition (as well as one or more flavorants, medicaments, or the like that may likewise be provided for delivery to a user) and form an aerosol for delivery to the user. When the heating element heats the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof. Additionally, the selection of various aerosol delivery device components can be appreciated upon consideration of the commercially available electronic aerosol delivery devices, such as those representative products listed in the background art section of the present disclosure.

An aerosol delivery device incorporates a battery or other electrical power source to provide current flow sufficient to provide various functionalities to the article, such as powering of a heater, powering of control systems, powering of indicators, and the like. The power source can take on various embodiments. Preferably, the power source is able to deliver sufficient power to rapidly heat the heating element to provide for aerosol formation and power the article through use for the desired duration of time. The power source preferably is sized to fit conveniently within the aerosol delivery device so that the aerosol delivery device can be easily handled; and additionally, a preferred power source is of a sufficiently light weight to not detract from a desirable smoking experience.

An aerosol delivery device can include a cartridge and a control body that can be permanently or detachably aligned in a functioning relationship. Various embodiments of engagement between the cartridge and the control body may be employed such as a threaded engagement, a press-fit engagement, an interference fit, a magnetic engagement, or the like. The aerosol delivery device may be substantially rod-like, substantially tubular shaped, or substantially cylindrically shaped in some embodiments when the cartridge and the control body are in an assembled configuration. However, various other shapes and configurations may be employed in other embodiments.

In specific embodiments, one or both of the cartridge and the control body may be referred to as being disposable or as being reusable. For example, the control body may have a replaceable battery or a rechargeable battery and thus may be combined with any type of recharging technology, including connection to a typical alternating current electrical outlet, connection to a car charger (i.e., cigarette lighter receptacle), and connection to a computer, such as through a universal serial bus (USB) cable. Further, in some embodiments the cartridge may comprise a single-use cartridge, as disclosed in U.S. Pat. Pub. No. 2014/0060555 to Chang et al., which is incorporated herein by reference in its entirety.

In some embodiments a cartridge may include a base that may comprise anti-rotation features that substantially prevent relative rotation between the cartridge and the control body as disclosed in U.S. patent application Ser. No. 13/840,264 to Novak et al., filed Mar. 15, 2013, which is incorporated herein by reference in its entirety.

An aerosol delivery device may include a component configured to hold an aerosol precursor composition. The aerosol precursor composition, also referred to as a vapor precursor composition, may comprise a variety of components including, by way of example, a polyhydric alcohol (e.g., glycerin, propylene glycol, or a mixture thereof), nicotine, tobacco, tobacco extract, and/or flavorants. Various components that may be included in the aerosol precursor composition are described in U.S. Pat. No. 7,726,320 to Robinson et al., which is incorporated herein by reference in its entirety. Additional representative types of aerosol precursor compositions are set forth in U.S. Pat. No. 4,793,365 to Sensabaugh, Jr. et al.; U.S. Pat. No. 5,101,839 to Jakob et al.; PCT WO 98/57556 to Biggs et al.; U.S. patent application Ser. No. 14/245,105 to Henry, Jr., filed Apr. 4, 2014; and Chemical and Biological Studies on New Cigarette Prototypes that Heat Instead of Burn Tobacco, R. J. Reynolds Tobacco Company Monograph (1988); the disclosures of which are incorporated herein by reference in their entireties.

A variety of heater components may be used in the present aerosol delivery device. In various embodiments, one or more microheaters or like solid state heaters may be used.

Embodiments of microheaters that may be utilized are further described herein. Further microheaters and atomizers incorporating microheaters suitable for use in the presently disclosed devices are described in U.S. Pat. Pub. No. 2014/0060554 to Collett et al., which is incorporated herein by reference in its entirety. In some embodiments a heating element may be formed by winding a wire about a liquid transport element as described in U.S. patent application Ser. No. 13/708,381 to Ward et al., filed Dec. 7, 2012, which is incorporated herein by reference in its entirety. Further, in some embodiments the wire may define a variable coil spacing, as described in U.S. patent application Ser. No. 13/827,994 to DePiano et al., filed Mar. 14, 2013, which is incorporated herein by reference in its entirety. Various embodiments of materials configured to produce heat when electrical current is applied therethrough may be employed to form a resistive heating element. Example materials from which the wire coil may be formed include Kanthal (Fe-CrAl), Nichrome, Molybdenum disilicide ($MoSi_2$), molybdenum silicide (MoSi), Molybdenum disilicide doped with Aluminum ($Mo(Si,Al)_2$), graphite and graphite-based materials; and ceramic (e.g., a positive or negative temperature coefficient ceramic). In further embodiments a stamped heating element may be employed in the atomizer, as described in U.S. patent application Ser. No. 13/842,125 to DePiano et al., filed Mar. 15, 2013, which is incorporated herein by reference in its entirety. Further to the above, additional representative heating elements and materials for use therein are described in U.S. Pat. No. 5,060,671 to Counts et al.; U.S. Pat. No. 5,093,894 to Deevi et al.; U.S. Pat. No. 5,224,498 to Deevi et al.; U.S. Pat. No. 5,228,460 to Sprinkel Jr., et al.; U.S. Pat. No. 5,322,075 to Deevi et al.; U.S. Pat. No. 5,353,813 to Deevi et al.; U.S. Pat. No. 5,468,936 to Deevi et al.; U.S. Pat. No. 5,498,850 to Das; U.S. Pat. No. 5,659,656 to Das; U.S. Pat. No. 5,498,855 to Deevi et al.; U.S. Pat. No. 5,530,225 to Hajaligol; U.S. Pat. No. 5,665,262 to Hajaligol; U.S. Pat. No. 5,573,692 to Das et al.; and U.S. Pat. No. 5,591,368 to Fleischhauer et al., the disclosures of which are incorporated herein by reference in their entireties. Further, chemical heating may be employed in other embodiments. Various additional examples of heaters and materials employed to form heaters are described in U.S. Pat. Pub. No. 2014/0060554 to Collett et al., which is incorporated herein by reference, as noted above.

In some embodiments the aerosol delivery devices of the present disclosure may include a control body and a cartridge. When the control body is coupled to the cartridge, an electronic control component in the cartridge may form an electrical connection with the control body. The control body may thus employ the electronic control component to determine whether the cartridge is genuine and/or perform other functions. Further, various examples of electronic control components and functions performed thereby are described in U.S. Pat. App. Pub. No. 2014/0096781 to Sears et al., which is incorporated herein by reference in its entirety.

During use, a user may draw on a mouthpiece of the cartridge of the aerosol delivery device. This may pull air through an opening in the control body or in the cartridge. For example, in one embodiment an opening may be defined between the coupler and the outer body of the control body, as described in U.S. patent application Ser. No. 13/841,233 to DePiano et al., filed Mar. 15, 2013, which is incorporated herein by reference in its entirety. However, the flow of air may be received through other parts of the aerosol delivery device in other embodiments.

A sensor in the aerosol delivery device (e.g., a puff or flow sensor in the control body) may sense the puff. When the puff is sensed, the control body may direct current to the heater through a circuit. Accordingly, the heater may vaporize the aerosol precursor composition, and the mouthpiece may allow passage of air and entrained vapor (i.e., the components of the aerosol precursor composition in an inhalable form) from the cartridge to a consumer drawing thereon.

Figure 3:
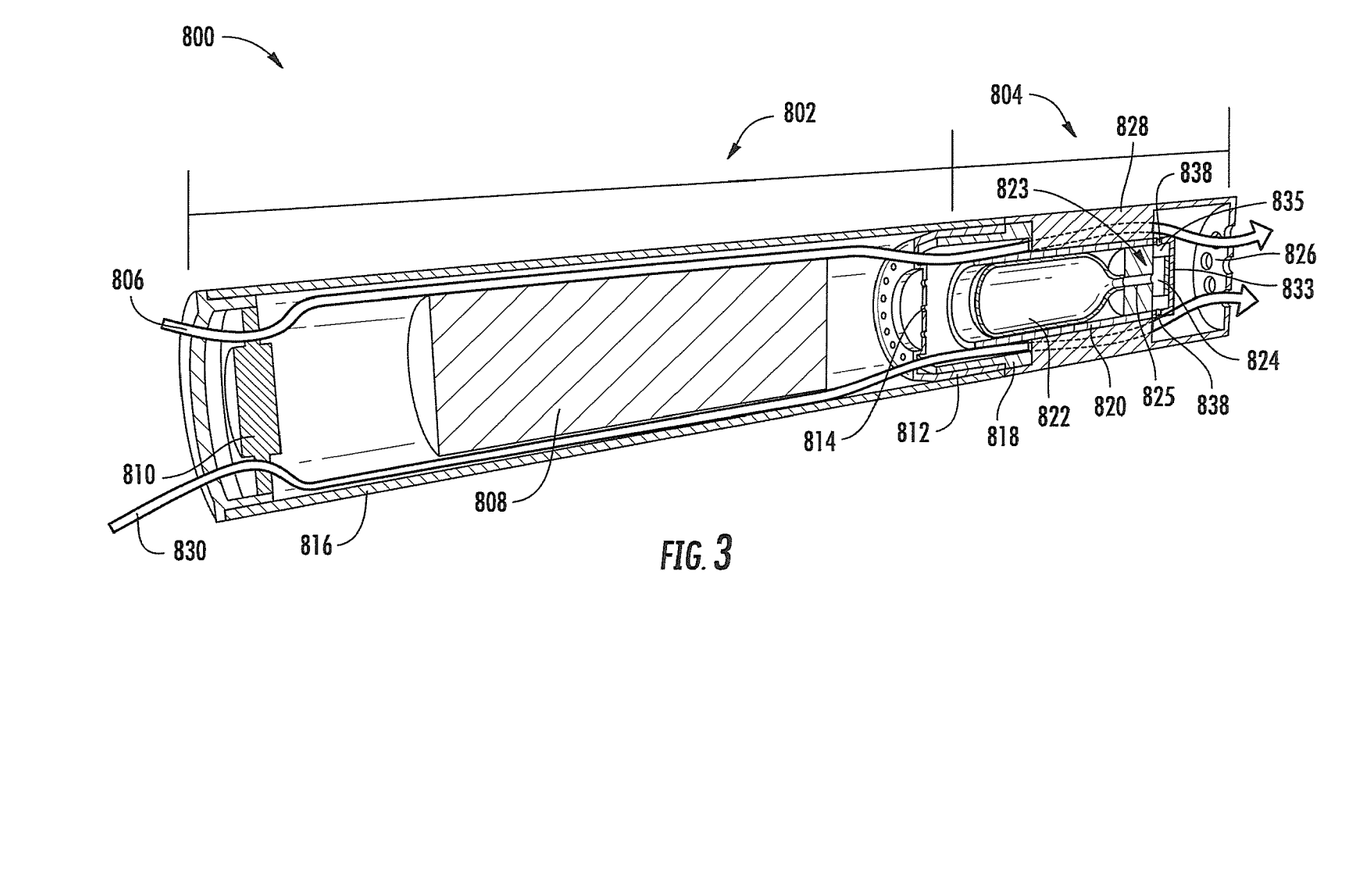
FIG. 3 illustrates an enlarged sectional view through the aerosol delivery device of FIG. 2 showing airflow therethrough according to an example embodiment of the present disclosure.
Figure 4:
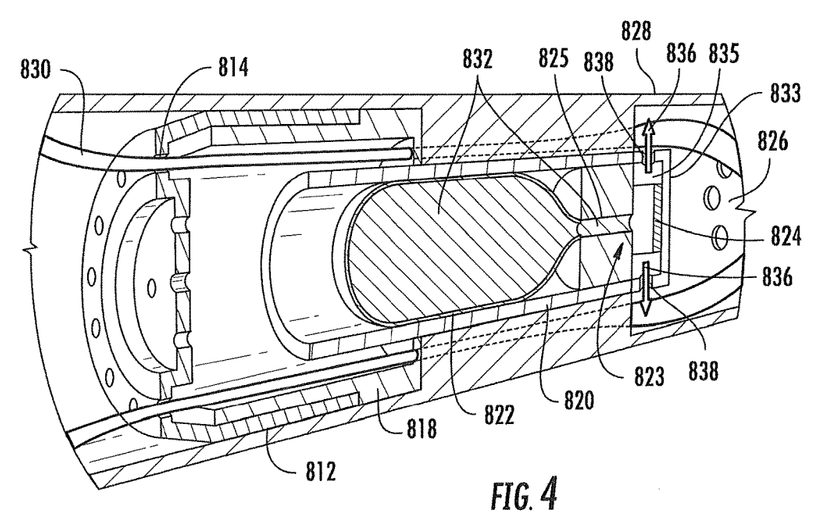
FIG. 4 illustrates an enlarged sectional view through the aerosol delivery device of FIG. 2 showing the aerosol precursor composition dispensing from the bag to an atomizer according to an example embodiment of the present disclosure.
Figure 5:
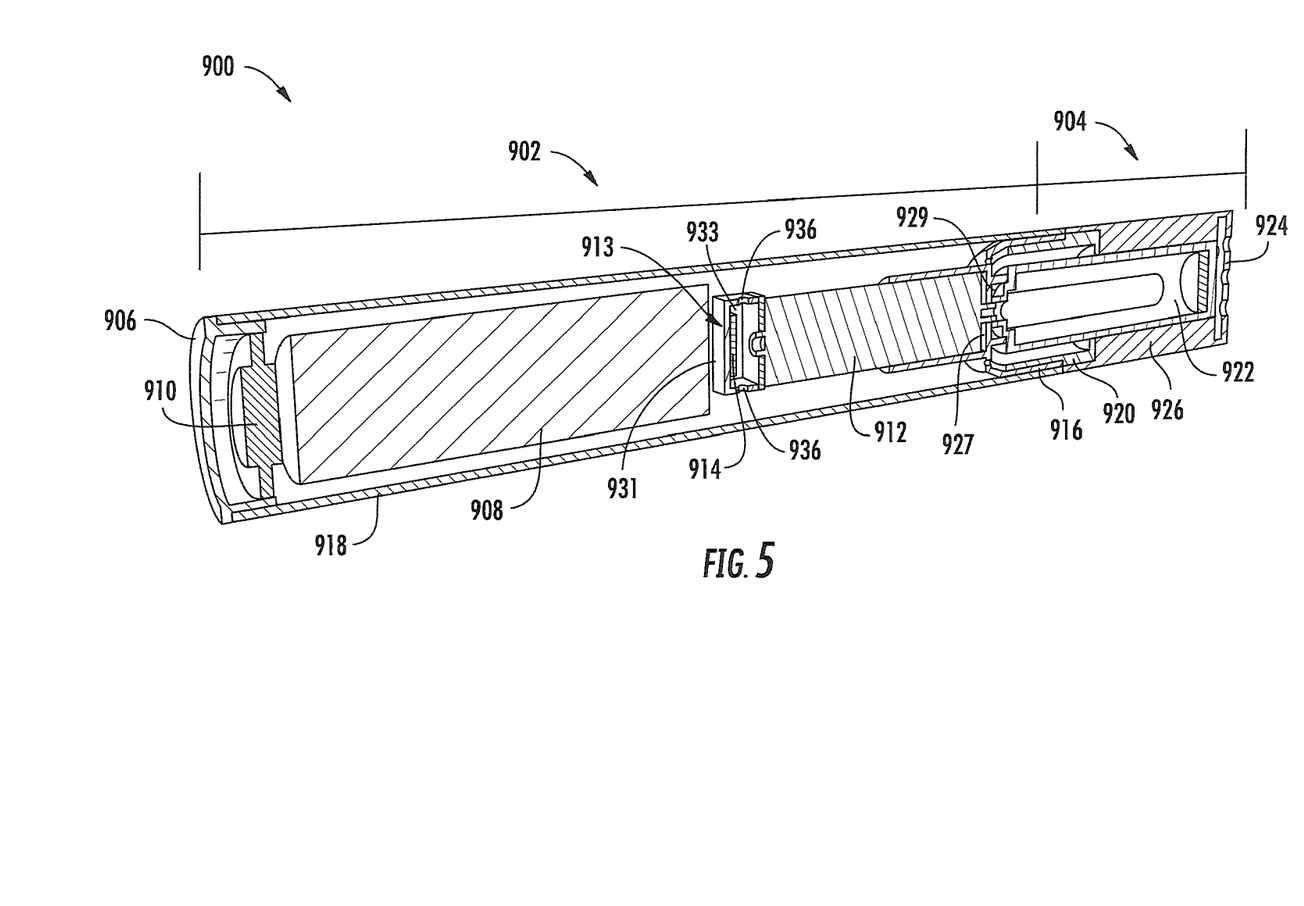
FIG. 5 illustrates a sectional view through an aerosol delivery device including a valve and a pressurized reservoir filled with an aerosol precursor composition according to an example embodiment of the present disclosure.

Various other details with respect to the components that may be included in the cartridge, are provided, for example, in U.S. patent application Ser. No. 13/840,264 to Novak et al., filed Mar. 15, 2013, which is incorporated herein by reference in its entirety. In this regard, FIG. 7 thereof illustrates an enlarged exploded view of a base and a control component terminal; FIG. 8 thereof illustrates an enlarged perspective view of the base and the control component terminal in an assembled configuration; FIG. 9 thereof illustrates an enlarged perspective view of the base, the control component terminal, an electronic control component, and heater terminals of an atomizer in an assembled configuration; FIG. 10 thereof illustrates an enlarged perspective view of the base, the atomizer, and the control component in an assembled configuration; FIG. 11 thereof illustrates an opposing perspective view of the assembly of FIG. 10 thereof; FIG. 12 thereof illustrates an enlarged perspective view of the base, the atomizer, the flow tube, and the reservoir substrate in an assembled configuration; FIG. 13 thereof illustrates a perspective view of the base and an outer body in an assembled configuration; FIG. 14 thereof illustrates a perspective view of a cartridge in an assembled configuration; FIG. 15 thereof illustrates a first partial perspective view of the cartridge of FIG. 14 thereof and a coupler for a control body; FIG. 16 thereof illustrates an opposing second partial perspective view of the cartridge of FIG. 14 thereof and the coupler of FIG. 11 thereof; FIG. 17 thereof illustrates a perspective view of a cartridge including a base with an anti-rotation mechanism; FIG. 18 thereof illustrates a perspective view of a control body including a coupler with an anti-rotation mechanism; FIG. 19 thereof illustrates alignment of the cartridge of FIG. 17 with the control body of FIG. 18; FIG. 3 thereof illustrates an aerosol delivery device comprising the cartridge of FIG. 17 thereof and the control body of FIG. 18 thereof with a modified view through the aerosol delivery device illustrating the engagement of the anti-rotation mechanism of the cartridge with the anti-rotation mechanism of the connector body; FIG. 4 thereof illustrates a perspective view of a base with an anti-rotation mechanism; FIG. 5 thereof illustrates a perspective view of a coupler with an anti-rotation mechanism; and FIG. 6 thereof illustrates a sectional view through the base of FIG. 4 thereof and the coupler of FIG. 5 thereof in an engaged configuration.

Various components of an aerosol delivery device according to the present disclosure can be chosen from components described in the art and commercially available. Reference is made for example to the reservoir and heater system for controllable delivery of multiple aerosolizable materials in an electronic smoking article disclosed in U.S. Pat. Pub. No. 2014/0000638 to Sebastian et al., which is incorporated herein by reference in its entirety.

Figure 1:
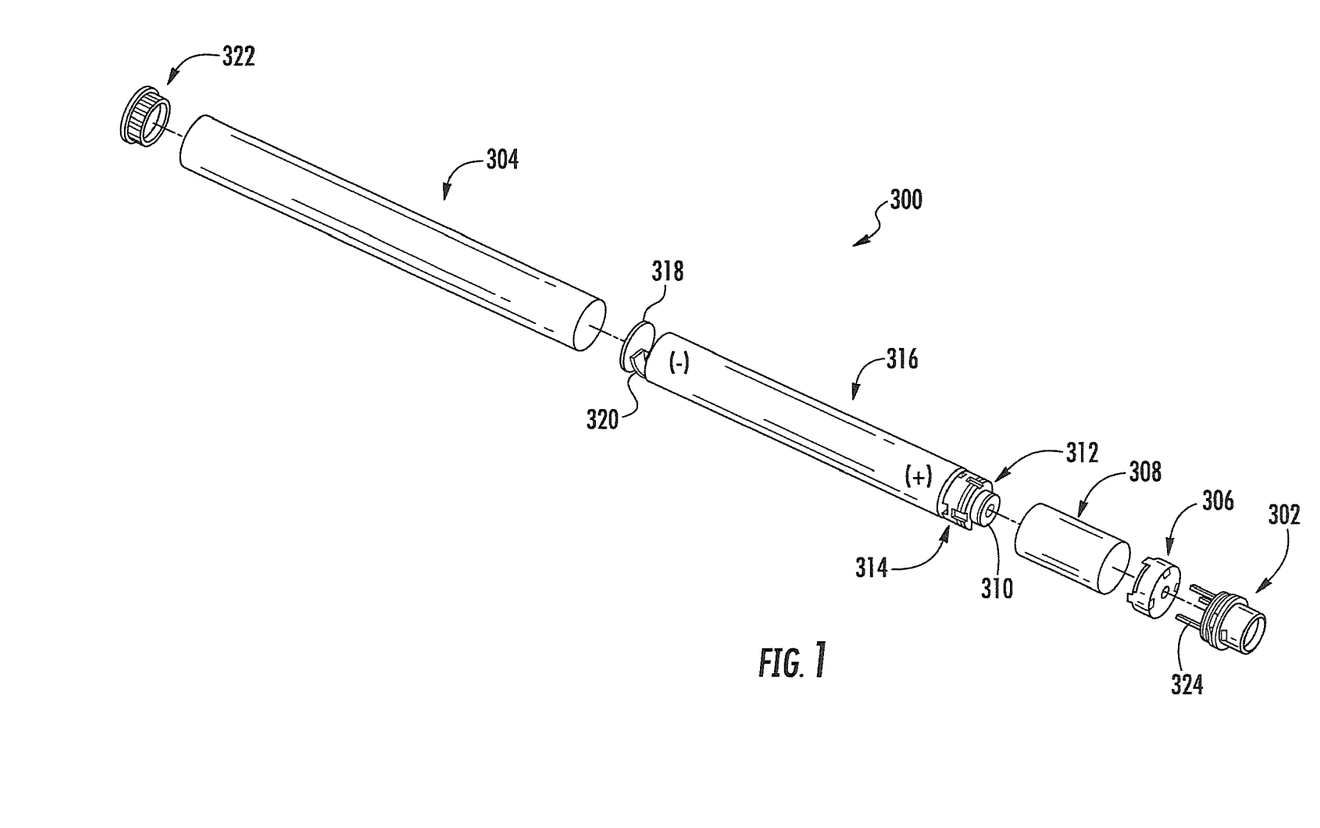
FIG. 1 illustrates an exploded view of a control body according to an example embodiment of the present disclosure.

FIG. 1 illustrates an exploded view of a control body 300 of an aerosol delivery device according to an example embodiment of the present disclosure. As illustrated, the control body 300 may comprise a coupler 302, an outer body 304, a sealing member 306, an adhesive member 308 (e.g., KAPTON® tape), a flow sensor 310 (e.g., a puff sensor or pressure switch), a control component 312, a spacer 314, an electrical power source 316 (e.g., a battery, which may be rechargeable), a circuit board with an indicator 318 (e.g., a light emitting diode (LED)), a connector circuit 320, and an end cap 322. Examples of electrical power sources are described in U.S. Pat. App. Pub. No. 2010/0028766 by Peckerar et al., the disclosure of which is incorporated herein by reference in its entirety. An exemplary mechanism that can provide puff-actuation capability includes a Model 163PC01D36 silicon sensor, manufactured by the Micro-Switch division of Honeywell, Inc., Freeport, Ill. Further examples of demand-operated electrical switches that may be employed in a heating circuit according to the present disclosure are described in U.S. Pat. No. 4,735,217 to Gerth et al., which is incorporated herein by reference in its entirety. Further description of current regulating circuits and other control components, including microcontrollers that can be useful in the present aerosol delivery device, are provided in U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., and U.S. Pat. No. 7,040,314 to Nguyen et al., all of which are incorporated herein by reference in their entireties. Reference also is made to the control schemes described in U.S. application Ser. No. 13/837,542 to Ampolini et al., filed Mar. 15, 2013, which is incorporated herein by reference in its entirety.

In one embodiment the indicator 318 may comprise one or more light emitting diodes. The indicator 318 can be in communication with the control component 312 through the connector circuit 320 and illuminate, for example, during a user drawing on a cartridge coupled to the coupler 302, as detected by the flow sensor 310. The end cap 322 may be adapted to make visible the illumination provided thereunder by the indicator 318. Accordingly, the indicator 318 may illuminate during use of the aerosol delivery device to simulate the lit end of a smoking article. However, in other embodiments the indicator 318 can be provided in varying numbers and can take on different shapes and can even be an opening in the outer body (such as for release of sound when such indicators are present).

Still further components can be utilized in the aerosol delivery device of the present disclosure. For example, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and WO 2010/003480 by Flick discloses a fluid flow sensing system indicative of a puff in an aerosol generating system; all of the foregoing disclosures being incorporated herein by reference in their entireties. Further examples of components related to electronic aerosol delivery articles and disclosing materials or components that may be used in the present article include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. App. Pub. Nos. 2006/0196518 and 2009/0188490 to Hon; U.S. Pat. App. Pub. No. 2009/0272379 to Thorens et al.; U.S. Pat. App. Pub. Nos. 2009/0260641 and 2009/0260642 to Monsees et al.; U.S. Pat. App. Pub. Nos. 2008/0149118 and 2010/0024834 to Oglesby et al.; U.S. Pat. App. Pub. No. 2010/0307518 to Wang; WO 2010/091593 to Hon; WO 2013/089551 to Foo; and U.S. patent application Ser. No. 13/841,233 to DePiano et al., filed Mar. 15, 2013, each of which is incorporated herein by reference in its entirety. A variety of the materials disclosed by the foregoing documents may be incorporated into the present devices in various embodiments, and all of the foregoing disclosures are incorporated herein by reference in their entireties.

Accordingly, example embodiments of aerosol delivery devices are described above. However, the present disclosure provides various other embodiments of aerosol delivery devices. As described hereinafter, such aerosol delivery devices may include differing configurations of components for storing, delivering, and/or vaporizing an aerosol precursor composition. For example, as illustrated in FIGS. 2-7 and described in the following text associated therewith, in some embodiments the aerosol precursor composition may be dispensed from a reservoir by a pressure differential, which may be controlled by various embodiments of pressure controllers.

Figure 2:
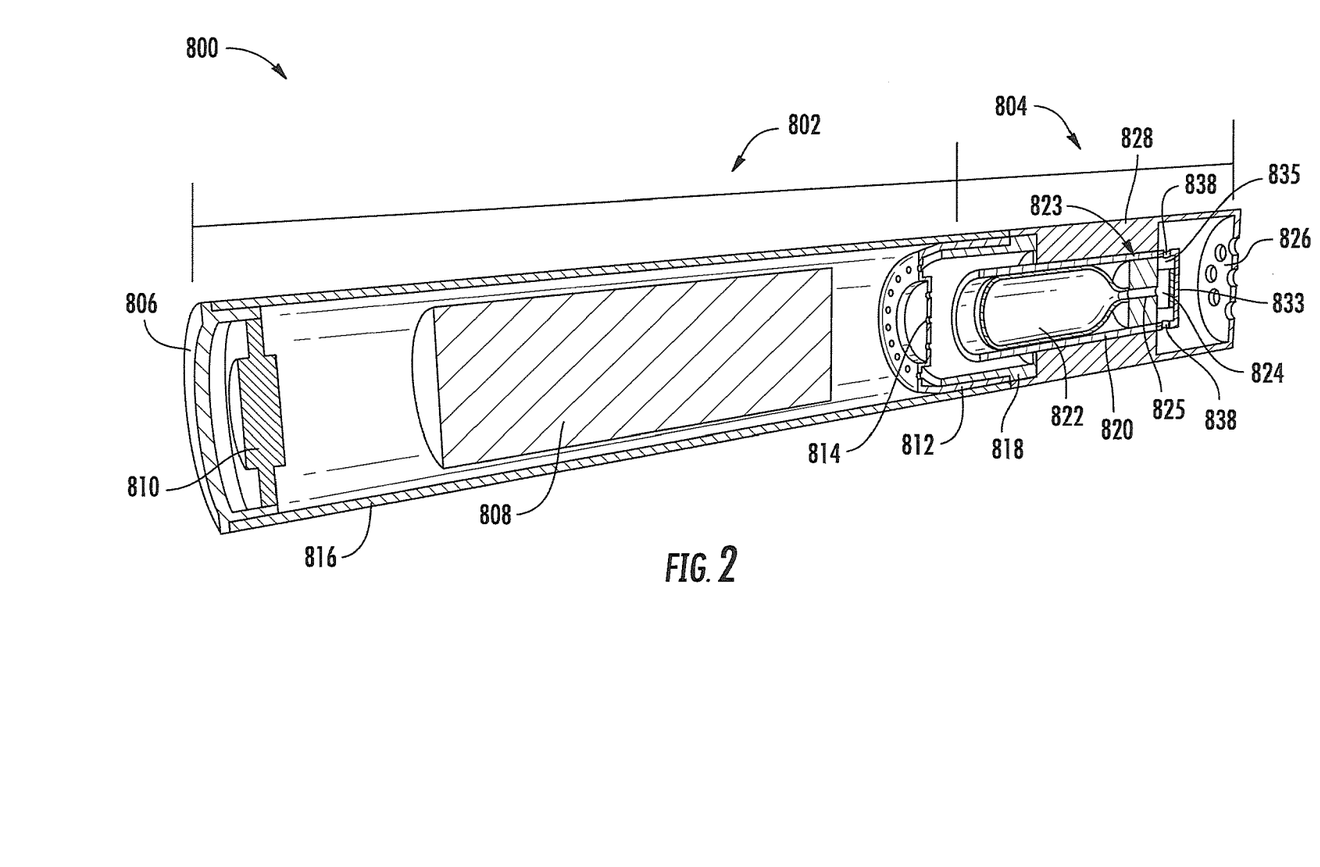
FIG. 2 illustrates a sectional view through an aerosol delivery device including bag filled with an aerosol precursor composition that is configured to passively dispense the aerosol precursor composition during a puff according to an example embodiment of the present disclosure.

In this regard, FIG. 2 illustrates a sectional view through an aerosol delivery device 800 according to an additional example embodiment of the present disclosure. As illustrated, the aerosol delivery device 800 may include a control body 802 and a cartridge 804. The control body 802 may include an indicator 806 (e.g., an LED), an electrical power source 808 (e.g., a battery, which may be rechargeable), a flow sensor 810, a coupler 812 including one or more restrictor apertures 814 defined therethrough, and an outer body 816. The cartridge 804 may include a base 818, a reservoir 820 that may include an aerosol precursor bag 822 received therein, an atomizer 823 comprising a heating element 824 and a fluid delivery tube 825, a mouthpiece 826, and an outer body 828. The base 818 of the cartridge 804 may be configured to releasably engage the coupler 812 of the control body 802 to form a mechanical and electrical connection therebetween.

FIG. 3 illustrates an additional sectional view through the aerosol delivery device 800. More particularly, FIG. 3 illustrates a flow path of air through the aerosol delivery device 800 when a user draws on the mouthpiece 826. As illustrated, an airflow or flow of ambient air 830 may enter the aerosol delivery device 800 and travel past the flow sensor 810. Although the ambient air 830 is illustrated as flowing past the electrical power source 808, in other embodiments the air may not flow past the electrical power source and/or the flow sensor may be positioned at an alternative location. The air 830 may then travel through the coupler 812 through the restrictor apertures 814 defined therethrough, through the base 818, around the reservoir 820, and out the mouthpiece 826.

As illustrated in FIG. 3, in one embodiment the air 830 may enter the aerosol delivery device 800 through a longitudinal end thereof, opposite from the mouthpiece 826. However, in other embodiments the air may enter the aerosol delivery device at an alternate location. For example, the air may enter through the coupler or the base, or at a location between the base and the mouthpiece. Accordingly, it should be understood that the particular airflow patterns described herein are provided for example purposes only.

As will be described below, an aerosol precursor composition 832 may be directed from the aerosol precursor bag 822 to the atomizer 823. In this regard, the atomizer 823 may comprise a housing 833 defining a chamber 835 in which the heating element 824 is positioned and to which the aerosol precursor composition 832 is delivered. Thus, issues with respect to the aerosol precursor composition 832 being directed into the air 830 and to a user without being vaporized may be avoided. In this regard, the aerosol precursor composition 832 may be directed into contact with the heating element 824 at the chamber 835 to ensure vaporization thereof.

When a user puffs on the mouthpiece 826 of the aerosol delivery device 800, a pressure differential may be created on opposing sides of the aerosol precursor bag 822. More particularly, restricted flow of the air 830 around the reservoir 820 may cause a portion of the aerosol delivery device 800 between the base 818 and the aerosol precursor bag 822 (e.g., within the control body 802) to have a relatively higher pressure than a portion of the aerosol delivery device between the aerosol delivery bag and the mouthpiece 826 (e.g., within the cartridge 804). In other embodiments, the pressure differential on opposing sides of the aerosol precursor bag may be formed in other manners wherein the pressure differential is employed to direct an aerosol precursor composition therefrom.

Although a pressure differential is described above as being defined between first and second opposing sides of the aerosol precursor bag 822 during a draw on the aerosol delivery device 800, a pressure differential may additionally or alternatively be defined between other locations. For example, a pressure differential may be defined between a first pressure within the reservoir 820 (and more particularly, within the aerosol precursor bag 822) and a second pressure proximate the atomizer 823 (and more particularly, proximate an outlet to the fluid delivery tube 825 within the chamber 835 defined by the housing 833) during a draw on the aerosol delivery device 800. In this regard, as a user draws on the mouthpiece 826, the pressure within the cartridge 804 may be reduced. Accordingly, the second pressure proximate the atomizer 823 may be reduced and may become less than the first pressure with the aerosol precursory bag 822. In this regard, in some embodiments the first pressure within the aerosol precursor bag 822 of the reservoir 820 may be substantially equal to an ambient pressure (e.g., atmospheric pressure). Thus, as a result of a sub-atmospheric pressure being defined proximate the outlet to the fluid delivery tube 825 at the atomizer 823 during a draw on the aerosol delivery device 800, the aerosol precursor composition 832 may be expelled from the aerosol precursor bag 822 through the fluid delivery tube to the heating element 824 during a draw on the mouthpiece 826.

However, in instances in which a small pressure drop is associated with the draw on the aerosol delivery device 800, the pressure differential between the first pressure in the aerosol precursor bag 822 and the second pressure proximate the atomizer 823 may be relatively small. In other words, when there is relatively little resistance to a draw on the aerosol delivery device 800, the decrease in pressure within the cartridge 804 relative to an atmospheric pressure may be relatively low. Accordingly, the aerosol delivery device 800 may include a pressure controller configured to produce the pressure differential.

In particular, the pressure controller may comprise a flow restrictor configured to restrict the airflow through the aerosol delivery device 800 in order to produce the pressure differential. Various embodiments of flow restrictors may be employed. For example, the flow restrictors may comprise the restrictor apertures 814 defined through the coupler 812. Thus, restrictor apertures 814 may define a relatively small area, which increases a pressure drop associated with air traveling from the control body 802 to the cartridge 804. In another embodiment, the restrictor apertures may be additionally or alternatively defined in the cartridge (e.g., through the base or around the reservoir) and function in substantially the same manner to increase the pressure drop associated with drawing on the aerosol delivery device. In other embodiments various other restrictions along the airflow path through the aerosol delivery device 800 may be employed.

Use of the aerosol precursor bag 822, as opposed to a rigid container, may assist in dispensing the aerosol precursor composition 832 from the reservoir 820. In this regard, the aerosol precursor bag 822 may collapse as the aerosol precursor composition 832 is dispensed therefrom. In one embodiment the aerosol precursor bag 822 may comprise an elastic material (e.g., rubber) that promotes the delivery of the aerosol precursor composition 832 therefrom while resisting formation of a vacuum therein. In this regard, the elastic material may be in slight tension when the aerosol precursor bag is filled with the aerosol precursor composition and may define a neutral state when empty. Accordingly, a vacuum may not be created in the reservoir 820 as the aerosol precursor composition 832 is dispensed, which may otherwise make it difficult to dispense the aerosol precursor composition without including features configured to vent the reservoir to allow for air entry thereto.

Regardless of the particular manner in which the pressure differential is formed and the particular embodiment of reservoir employed, the pressure differential may cause the aerosol precursor composition 832 to be expelled through the fluid delivery tube 825 to the atomizer 823 at which the heating element 824 vaporizes the aerosol precursor composition, as illustrated in FIG. 4. In this regard, when the flow sensor 810 detects a puff on the aerosol delivery device 800, current from the electrical power source 808 may be directed to the atomizer 823 to produce heat. Accordingly, as illustrated in FIG. 4, the aerosol precursor composition 832 directed to the atomizer 823 may be heated and vaporized. The aerosol or vapor 836 formed in the chamber 835 may then mix with the air 830 and exit through the mouthpiece 826.

The chamber 835 may be configured to provide for optimal rates of release of the vapor 836 therefrom and into the air 830. In this regard, as illustrated in FIGS. 2-4, the chamber 835 may include one or more outlet apertures 838. As illustrated in FIG. 4, the vapor 836 may exit the chamber 933 through the outlet apertures 838.

Further, in one embodiment the chamber may additionally define one or more inlet apertures. The inlet apertures may be configured to allow flow of air therethough into the chamber. Thus, as a user draws on the aerosol delivery device, air entering through the inlet apertures may mix with the vapor and exit through the outlet apertures. In this regard, the inlet apertures may be positioned such that air flowing through the aerosol delivery device is incident upon the inlet apertures (e.g., the inlet apertures may extend substantially parallel to a longitudinal axis of the aerosol delivery device and hence substantially parallel to the airflow therethrough). Thus, the inlet apertures may assist in removing the vapor from the chamber.

Further, in some embodiments valves may be provided at one or both of the inlet apertures and the outlet apertures. Such valves may passively or actively open and close to allow flow of air into the chamber and/or allow flow of vapor out of the chamber. Alternatively or additionally, the inlet apertures and/or the outlet apertures may be particularly sized to provide a desired flow of the vapor from the chamber while ensuring substantially complete vaporization of the aerosol precursor composition.

Although the fluid delivery tube 825 allows flow of the aerosol precursor composition 832 therethrough when a pressure differential is applied in order to produce the vapor 836 as described above, in other instances (e.g., at other times) the fluid delivery tube may resist flow of the aerosol precursor composition to the heating element 824. In this regard, the fluid delivery tube may be sized such that flow therethough is resisted when the pressure differential is not present. For example, surface tension may resist flow therethrough. Accordingly, the dimensions of the fluid delivery tube 825 may be particularly selected to resist flow therethough, in instances other than when the pressure differential is applied, based on the viscosity of the aerosol precursor composition 832.

FIG. 5 illustrates a sectional view through an aerosol delivery device 900 according to an additional example embodiment of the present disclosure. The aerosol delivery device 900 may employ a differing embodiment of a pressure controller to produce a pressure differential, as described below. As illustrated, the aerosol delivery device 900 may include a control body 902 and a cartridge 904. The control body 902 may include an indicator 906 (e.g., an LED), an electrical power source 908 (e.g., a battery, which may be rechargeable), a flow sensor 910, an active valve 912 (e.g., a micro pressure valve), an atomizer 914 (e.g., comprising a heating element), a coupler 916, and an outer body 918. The cartridge 904 may include a base 920, a pressurized reservoir 922, a mouthpiece 924, and an outer body 926. The base 920 of the cartridge 904 may be configured to releasably engage the coupler 916 of the control body 902 to form a mechanical and electrical connection therebetween. Thus, the active valve 912 may be in fluid communication with the pressurized reservoir 922 when the coupler 916 of the control body 902 is coupled to the base 920 of the cartridge 904. For example, as illustrated, the active valve 912 may define an extension 927 configured to engage a recess 929 in the pressurized reservoir 922. However, various other connection components and methods may be employed in other embodiments, so long as the mechanism is configured to provide a substantially fluid-tight seal that resists pressure loss from the pressurized reservoir 922 other than that which occurs when the active valve 912 opens, as described below.

Figure 6:
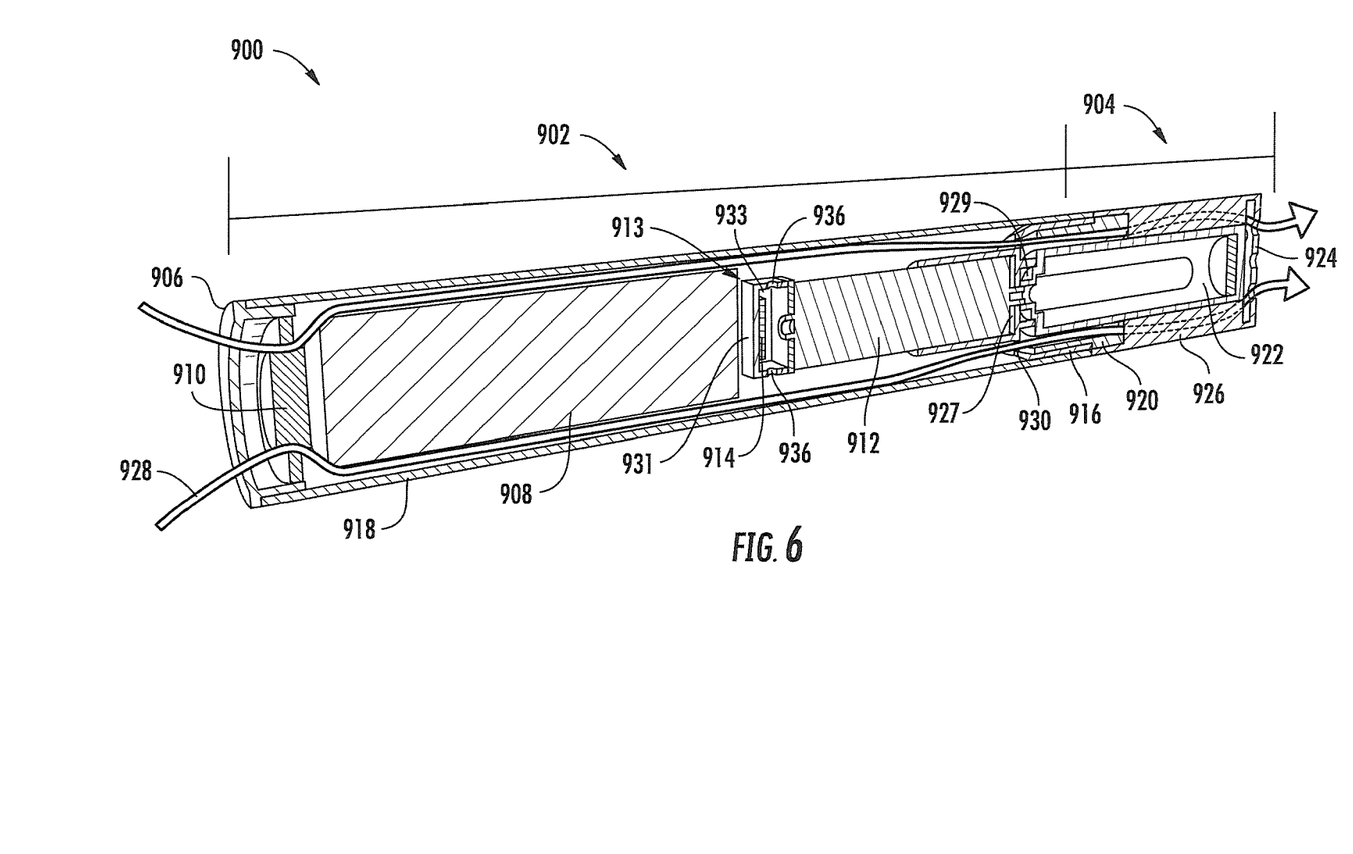
FIG. 6 illustrates a sectional view through the aerosol delivery device of FIG. 5 showing airflow therethrough according to an example embodiment of the present disclosure.

FIG. 6 illustrates an additional sectional view through the aerosol delivery device 900. More particularly, FIG. 6 illustrates a flow path of air through the aerosol delivery device 900 when a user draws on the mouthpiece 924. As illustrated, an airflow or flow of ambient air 928 may enter the aerosol delivery device 900 and travel past the flow sensor 910. Although the ambient air 928 is illustrated as flowing past the electrical power source 908, in other embodiments the air may not flow past the electrical power source and/or the flow sensor may be positioned at an alternative location. The air 928 may then travel through the coupler 916 through one or more apertures 930 defined therethrough, through the base 920, around the pressurized reservoir 922, and out the mouthpiece 924.

As illustrated in FIG. 6, in one embodiment the air 928 may enter the aerosol delivery device 900 through a longitudinal end thereof, opposite from the mouthpiece 924. However, in other embodiments the air may enter the aerosol delivery device at an alternate location. For example, the air may enter through the coupler or the base, or at a location between the base and the mouthpiece. Accordingly, it should be understood that the particular airflow patterns described herein are provided for example purposes only.

The aerosol delivery device 900 may include a pressure controller configured to control dispensing of the aerosol precursor composition from the pressurized reservoir 922 based on a pressure differential between a first pressure within the reservoir 922 and a second pressure proximate the atomizer 913. However, whereas the embodiment of the aerosol delivery device 800 described above and illustrated in FIGS. 2-4 passively dispensed the aerosol precursor composition based on a pressure differential caused by a user draw thereon, the aerosol delivery device 900 illustrated in FIGS. 5-7 may employ the active valve 912 to selectively release the aerosol precursor composition from the reservoir 922 based on a preexisting pressure differential. In this regard, a first pressure within the pressurized reservoir 922 may be greater than an ambient pressure (e.g., atmospheric pressure) and hence also greater than a second pressure proximate the atomizer 913. In other words, the reservoir 922 may be pressurized.

The reservoir 922 may be pressurized in a variety of manners. For example, carbon dioxide, air, or other compressible fluid may be introduced into the reservoir 922 at a positive pressure in addition to the aerosol precursor composition. By way of further example, a piston and a compressed spring within the reservoir may be configured to force the aerosol precursor composition therefrom.

Figure 7:
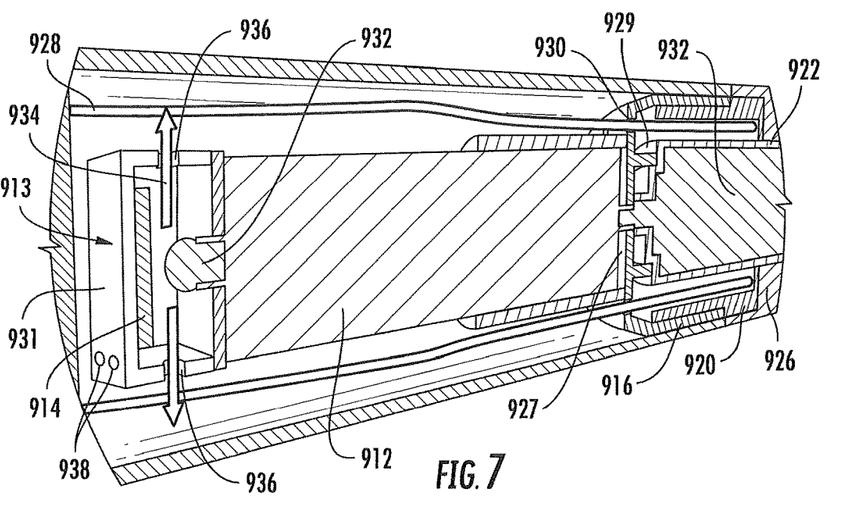
FIG. 7 illustrates an enlarged sectional view through the aerosol delivery device of FIG. 5 showing the valve dispensing the aerosol precursor composition to an atomizer according to an example embodiment of the present disclosure.
Figure 8:
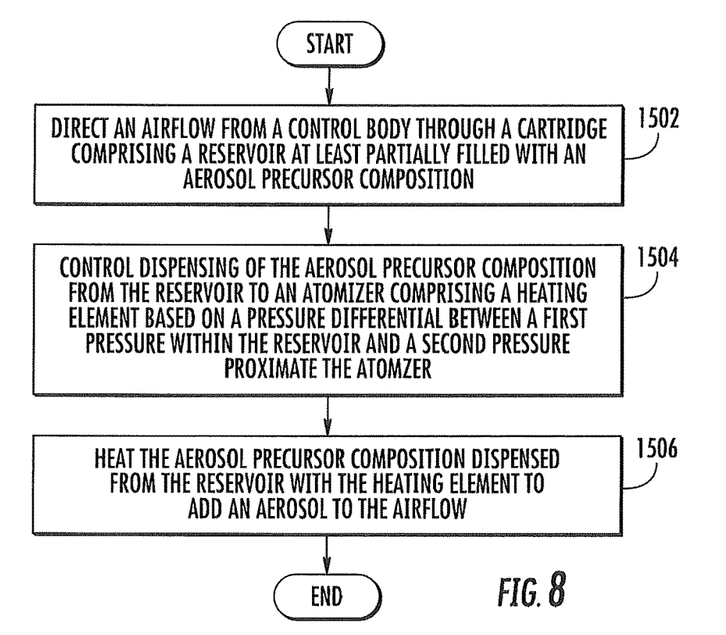
FIG. 8 schematically illustrates a method for aerosolization with an aerosol delivery device including dispensing an aerosol precursor composition with a pressure differential.

FIG. 7 illustrates an enlarged partial sectional view through the aerosol delivery device 900. As illustrated, when the flow sensor 910 (see, e.g., FIG. 6) detects the puff, current may be applied to the active valve 912, such that the active valve momentarily opens one or more times. For example, a signal from the flow sensor 910 may directly cause the active valve 912 to actuate, or the signal from the flow sensor may be provided to a controller which directs the active valve to actuate. Thereby, an aerosol precursor composition 932 retained in the pressurized reservoir 922 may be expelled toward the heating element 914 of the atomizer 913, as a result of the air proximate the atomizer being at a relatively lower pressure than the pressurized reservoir. Further, the atomizer 913 may comprise a housing 931 defining a chamber 933 (see, e.g., FIG. 6) in which the heating element 914 is positioned and to which the aerosol precursor composition 932 is delivered. Thus, issues with respect to the aerosol precursor composition 932 being directed into the air 928 and to a user without being vaporized may be avoided. In this regard, the aerosol precursor composition 932 may be directed into contact with the heating element 914 at the chamber 933 to ensure vaporization thereof.

In this regard, when the flow sensor 910 detects a puff on the aerosol delivery device 900, current from the electrical power source 908 may be directed to the heating element 914 to produce heat. Accordingly, the aerosol precursor composition 932 directed thereto may be heated and vaporized to define an aerosol or vapor 934. The vapor 934 may be formed in the chamber 933 and then exit therefrom. The vapor 934 may then mix with the air 928 and exit through the mouthpiece 924.

The chamber 933 may be configured to provide for optimal rates of release of the vapor 934 therefrom and into the air 928. In this regard, as illustrated in FIGS. 5-7, the chamber 933 may include one or more outlet apertures 936. As illustrated in FIG. 7, the vapor 934 may exit the chamber 933 through the outlet apertures 936.

Further, as illustrated in FIG. 7, in one embodiment the chamber 933 may additionally define one or more inlet apertures 938. The inlet apertures 938 may be configured to allow flow of air 928 therethough into the chamber 933. Thus, as a user draws on the aerosol delivery device 900, air 928 entering through the inlet apertures 938 may mix with the vapor 934 and exit through the outlet apertures 936. In this regard, as illustrated, the inlet apertures 938 may be positioned such that air 928 flowing through the aerosol delivery device 900 is incident upon the inlet apertures 938 (e.g., the inlet apertures may extend substantially parallel to a longitudinal axis of the aerosol delivery device and hence substantially parallel to the airflow therethrough). Thus, the inlet apertures 928 may assist in removing the vapor 934 from the chamber 933.

Further, in some embodiments valves may be provided at one or both of the inlet apertures 938 and the outlet apertures 936. Such valves may passively or actively open and close to allow flow of air 928 into the chamber 933 and/or allow flow of vapor 934 out of the chamber. Alternatively or additionally, the inlet apertures 938 and/or the outlet apertures 936 may be particularly sized to provide a desired flow of the vapor 934 from the chamber 933 while ensuring substantially complete vaporization of the aerosol precursor composition.

Note that various embodiments of atomizers may be employed to vaporize the aerosol precursor composition in the embodiments of aerosol delivery devices described above. Such atomizers may include flat heaters, wound wire surfaces, micro heaters (e.g., embodied on a chip) glass plates, lasers, resistive heaters, and any other shape and embodiment of heater. Further, the materials employed in the first heating elements and the second heating elements may vary. For example, the materials described above with respect to wire coil heating elements may be employed. Various other materials which may be employed in the heating elements described herein may include platinum or a platinum-coated materials and resistive inks (e.g., printed on a ceramic material).

Certain aerosol delivery devices described herein may avoid certain issues associated with conventional aerosol delivery devices that employ a wick. In this regard, use of a wick may cause separation of the ingredients of an aerosol precursor composition. Further, use of a wick to transfer the aerosol precursor composition from a substrate to a heating element may result in leakage. Accordingly, the embodiments of the aerosol delivery devices disclosed herein may provide these and/or other advantages.

As noted above, embodiments of aerosol delivery devices of the present disclosure may include a cartridge and a control body. Although the aerosol delivery devices have been described such that certain components thereof are positioned within the control body whereas other components are positioned within the cartridge, it should be understood that these configurations are provided for example purposes only. In this regard, any of the components of the aerosol delivery devices may be positioned within the cartridge or the control body. However, it may generally be desirable to position the reservoir within the cartridge such that the cartridge may be easily replaced or refilled by detaching the cartridge from the control body.

Note also that while the aerosol delivery devices disclosed herein are generally described as including a cartridge (e.g., a replaceable cartridge) and a control body (e.g., a reusable control body), various other embodiments may be employed. For example, in other embodiments the aerosol delivery devices may include more than two-pieces. In an additional embodiment the aerosol delivery device may define an integral, one-piece configuration.

In an additional embodiment a method for aerosolization in an aerosol delivery device is provided. As illustrated in FIG. 8, the method may include directing an airflow from a control body through a cartridge comprising a reservoir at least partially filled with an aerosol precursor composition at operation 1502. Further, the method may include controlling dispensing of the aerosol precursor composition from the reservoir to an atomizer comprising a heating element based on a pressure differential between a first pressure within the reservoir and a second pressure proximate the atomizer at operation 1504. The method may additionally include heating the aerosol precursor composition dispensed from the reservoir with the heating element to add an aerosol to the airflow at operation 1506.

In some embodiments of the method the first pressure within the reservoir may be greater than an ambient pressure (e.g., atmospheric pressure). Additionally, controlling dispensing of the aerosol precursor composition at operation 1504 may comprise selectively releasing the aerosol precursor composition from the reservoir with a valve. Further, the method may include detecting an airflow with a flow sensor. Controlling dispensing of the aerosol precursor composition at operation 1504 may comprise actuating the valve in response to a signal from the flow sensor. Selectively releasing the aerosol precursor composition from the reservoir with the valve may comprise directing the aerosol precursor composition from the reservoir in the cartridge through the valve in the control body.

In some embodiments an internal pressure within the reservoir may be substantially equal to an ambient pressure (e.g., atmospheric pressure). Additionally, controlling dispensing of the aerosol precursor composition at operation 1504 may comprise producing the pressure differential between the first pressure within the reservoir and the second pressure proximate the atomizer with a flow restrictor. The method may further comprise delivering the aerosol precursor composition through a fluid delivery tube to the heating element during application of the pressure differential and otherwise resisting flow of the aerosol precursor composition to the heating element. Controlling dispensing of the aerosol precursor composition at operation 1504 may comprise directing the aerosol precursor composition to a chamber of the atomizer in which the heating element is positioned.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

What is claimed is:

1. An aerosol delivery device, comprising:
a control body;
a cartridge comprising a reservoir at least partially filled with an aerosol precursor composition, the cartridge being configured to receive an airflow from the control body;
a mouthpiece;
an opening configured to receive the airflow,
an atomizer comprising a chamber and a heating element, the heating element being positioned within the chamber; and
a pressure controller configured to control dispensing of the aerosol precursor composition from the reservoir based on a pressure differential between a first pressure within the reservoir and a second pressure proximate the atomizer,
the atomizer being configured to heat the aerosol precursor composition received from the reservoir by direct contact with the heating element to produce an aerosol in the chamber, the aerosol exiting the chamber before being added to the airflow;
wherein the atomizer is positioned between and spaced apart from the opening and the mouthpiece along a longitudinal axis of the aerosol delivery device such that the opening receives the airflow upstream of the atomizer.

2. The aerosol delivery device of claim 1, wherein the first pressure within the reservoir is greater than an ambient pressure.

3. The aerosol delivery device of claim 2, wherein the pressure controller comprises a valve configured to selectively release the aerosol precursor composition from the reservoir.

4. The aerosol delivery device of claim 3, further comprising a flow sensor, wherein the valve is configured to actuate in response to a signal from the flow sensor.

5. The aerosol delivery device of claim 3, wherein the cartridge includes the valve and the atomizer.

6. The aerosol delivery device of claim 3, wherein the control body includes the valve and the atomizer.

7. The aerosol delivery device of claim 6, wherein the control body comprises a coupler and the cartridge comprises a base, the valve being in fluid communication with the reservoir when the coupler of the control body is coupled to the base of the cartridge.

8. The aerosol delivery device of claim 1, wherein the first pressure within the reservoir is substantially equal to an ambient pressure.

9. The aerosol delivery device of claim 8, wherein the pressure controller comprises a flow restrictor configured to produce the pressure differential between the first pressure within the reservoir and the second pressure proximate the atomizer.

10. The aerosol delivery device of claim 9, wherein the control body includes the flow restrictor.

11. The aerosol delivery device of claim 9, wherein the flow restrictor comprises one or more restrictor apertures.

12. The aerosol delivery device of claim 8, wherein the reservoir comprises an aerosol precursor bag.

13. The aerosol delivery device of claim 8, wherein the atomizer further comprises a fluid delivery tube configured to deliver the aerosol precursor composition from the reservoir to the heating element during application of the pressure differential and otherwise resist flow of the aerosol precursor composition to the heating element.

14. The aerosol delivery device of claim 1, wherein the cartridge comprises the mouthpiece.

15. A method for aerosolization in an aerosol delivery device, comprising:
directing an airflow from a control body through a cartridge comprising a reservoir at least partially filled with an aerosol precursor composition;
controlling dispensing of the aerosol precursor composition from the reservoir to an atomizer comprising a chamber and a heating element positioned within the chamber based on a pressure differential between a first pressure within the reservoir and a second pressure proximate the atomizer; and
heating the aerosol precursor composition dispensed from the reservoir into contact with the heating element to produce an aerosol in the chamber, the aerosol exiting the chamber before being added to the airflow,
wherein directing the airflow from the control through the cartridge comprises directing the airflow into an opening, through the control body, into the cartridge, and out through a mouthpiece,
wherein the atomizer is positioned between and spaced apart from the opening and the mouthpiece along a longitudinal axis of the aerosol delivery device such that the opening receives the airflow upstream of the atomizer.

16. The method of claim 15, wherein the first pressure within the reservoir is greater than an ambient pressure, and
wherein controlling dispensing of the aerosol precursor composition comprises selectively releasing the aerosol precursor composition from the reservoir with a valve.

17. The method of claim 16, further comprising detecting an airflow with a flow sensor,
wherein controlling dispensing of the aerosol precursor composition comprises actuating the valve in response to a signal from the flow sensor.

18. The method of claim 16, wherein selectively releasing the aerosol precursor composition from the reservoir with the valve comprises directing the aerosol precursor composition from the reservoir in the cartridge through the valve in the control body.

19. The method of claim 15, wherein an internal pressure within the reservoir is substantially equal to an ambient pressure, and
wherein controlling dispensing of the aerosol precursor composition comprises producing the pressure differential between the first pressure within the reservoir and the second pressure proximate the atomizer with a flow restrictor.

20. The method of claim 19, further comprising delivering the aerosol precursor composition through a fluid delivery tube to the heating element during application of the pressure differential and otherwise resisting flow of the aerosol precursor composition to the heating element.

* * * * *